US010653329B2

(12) United States Patent
Oh et al.

(10) Patent No.: US 10,653,329 B2
(45) Date of Patent: May 19, 2020

(54) PLANAR NEURAL PROBE STRUCTURE AND ITS ASSEMBLY STRUCTURE FOR CHRONIC IMPLANTATION

(71) Applicant: KOREA INSTITUTE OF SCIENCE AND TECHNOLOGY, Seoul (KR)

(72) Inventors: Sang Rok Oh, Gangneung-si (KR); Keehoon Kim, Seoul (KR); Sehyuk Yim, Seoul (KR); Yong Seok Ihn, Seoul (KR); Donghyun Hwang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 368 days.

(21) Appl. No.: 15/721,217

(22) Filed: Sep. 29, 2017

(65) Prior Publication Data
US 2018/0125427 A1     May 10, 2018

(30) Foreign Application Priority Data

Nov. 10, 2016  (KR) .......................... 10-2016-0149218

(51) Int. Cl.
*A61B 5/04*     (2006.01)
*A61N 1/05*     (2006.01)
*A61B 5/00*     (2006.01)

(52) U.S. Cl.
CPC ........ *A61B 5/04001* (2013.01); *A61B 5/6877* (2013.01); *A61N 1/0556* (2013.01); *A61N 1/0558* (2013.01); *A61B 2562/0209* (2013.01)

(58) Field of Classification Search
CPC  A61B 5/04001; A61B 5/6877; A61N 1/0551; A61N 1/0556; A61N 1/0558
See application file for complete search history.

(56) References Cited

U.S. PATENT DOCUMENTS

| 6,533,732 B1 | 3/2003 | Urmey |
| 8,359,083 B2 | 1/2013 | Clark et al. |
| 9,087,742 B2 * | 7/2015 | Cheng ................ A61B 5/04001 |

(Continued)

FOREIGN PATENT DOCUMENTS

| DE | 102004031377 | * | 2/2006 |
| JP | 2001-157669 A | | 6/2001 |

(Continued)

OTHER PUBLICATIONS

Branner et al., "Long-Term Stimulation and Recording With a Penetrating Microelectrode Array in Cat Sciatic Nerve", IEEE Transactions on Biomedical Engineering, Jan. 2004, vol. 51, No. 1, pp. 146-157.

*Primary Examiner* — Lee S Cohen
(74) *Attorney, Agent, or Firm* — Birch, Stewart, Kolasch & Birch, LLP (57) ABSTRACT

A neural probe structure, which is fixed to a nerve to acquire an electrical signal from the nerve or apply electrical stimulation to the nerve, includes a body which is bent to enclose at least a part of circumference of the nerve, and a probe which extends longitudinally from the body and passes through the nerve, wherein the probe has electrodes. A neural probe assembly includes the neural probe structure, wherein the probe passes through the nerve and the body encloses at least a part of circumference of the nerve, so that the neural probe structure is fixed to the nerve.

15 Claims, 10 Drawing Sheets

(56) References Cited

U.S. PATENT DOCUMENTS

| | | | |
|---|---|---|---|
| 9,247,889 B2* | 2/2016 | Yoon | A61B 5/04001 |
| 9,801,559 B2* | 10/2017 | Jamieson | A61B 5/6848 |
| 2004/0006281 A1 | 1/2004 | Matsukawa et al. | |
| 2010/0029148 A1* | 2/2010 | Perlin | A61B 5/04001 |
| | | | 439/884 |
| 2013/0072808 A1* | 3/2013 | Neves | A61B 5/685 |
| | | | 600/544 |
| 2016/0235329 A1* | 8/2016 | Bernstein | A61B 8/48 |
| 2017/0172437 A1* | 6/2017 | Butera | A61B 5/6877 |

FOREIGN PATENT DOCUMENTS

| | | | |
|---|---|---|---|
| JP | 2003-204946 A | | 7/2003 |
| JP | 2008-188123 A | | 8/2008 |
| KR | 10-2011-0090703 A | | 8/2011 |
| KR | 10-2012-0052633 A | | 5/2012 |
| KR | 10-1159252 B1 | | 6/2012 |
| KR | 10-2014-0133202 A | | 11/2014 |
| WO | WO2015/120222 | * | 8/2015 |
| WO | WO2016005400 | * | 1/2016 |

* cited by examiner

PLANAR NEURAL PROBE STRUCTURE AND ITS ASSEMBLY STRUCTURE FOR CHRONIC IMPLANTATION

CROSS-REFERENCE TO RELATED APPLICATION

This application claims priority to Korean Patent Application No. 10-2016-0149218, filed on Nov. 10, 2016, and all the benefits accruing therefrom under 35 U.S.C. § 119, the contents of which in its entirety are herein incorporated by reference.

BACKGROUND

1. Field

The present disclosure relates to a neural probe structure and its assembly structure. More particularly, the present disclosure relates to a planar neural probe structure that is fixed to a nerve to acquire an electrical signal from the nerve or apply electrical stimulation to the nerve, and its assembly structure for chronic implantation.

DESCRIPTION ABOUT NATIONAL RESEARCH AND DEVELOPMENT SUPPORT

This study was supported by Advanced Convergence Technology Development Project of National Research Foundation of Korea (Project Name: Development of bio-signal measurement and analysis system for movement and tactile transmission, and bionic arm with bio-signal-based control function, Project No. 1711042768) under the superintendence of Ministry of Science and ICT, Republic of Korea.

2. Description of the Related Art

Recently, studies are being intensively conducted to understand how nerve work by stimulating the nerve of a subject, and detecting and analyzing signals in response thereto.

To directly stimulate the nerve of the subject and collect its information, a neural probe structure that can be inserted into the subject is used.

The neural probe structure according to the related art is fixed in reliance on a probe which is in practice inserted into the nerve, and there is a limitation in fixing the neural probe structure to the nerve by the supporting strength of the thin, pointed probe.

The neural probe structure easily slips off when pulled in the insertion direction of the probe. To prevent this, a method which forms protrusions on the probe in the opposite direction is used, but this sharp structure may cause great damage to the nerve.

Moreover, even though the neural probe structure does not slip off, if the neural probe structure is subjected to forces when fixed to the nerve, serious damage may occur to the nerve due to the probe.

RELATED LITERATURES

Patent Literatures (Patent Literature 1) Korean Patent No. 10-1159252

SUMMARY

The present disclosure is designed to solve the problem of the related art, and therefore, the present disclosure is directed to providing a neural probe structure that can be fixed very firmly and stably to a nerve, and a neural probe assembly having the same.

To achieve the object, according to an aspect of the present disclosure, there is provided a neural probe structure which is fixed to a nerve to acquire an electrical signal from the nerve or apply electrical stimulation to the nerve, the neural probe structure including a body which is bent to enclose at least a part of circumference of the nerve, and a probe which extends longitudinally from the body and passes through the nerve, wherein the probe has electrodes.

According to an embodiment, the neural probe structure includes a plurality of probes, and the probes are each arranged in rows side by side in a widthwise direction of the body.

According to an embodiment, the body has a shape of a thin flat plate, and the neural probe structure is fixed to the nerve such that one side surface defining a thickness of the body stands facing a circumferential surface of the nerve.

According to an embodiment, the body of the neural probe structure has a polygonal shape with one open side, and the polygon has rounded corners.

According to an embodiment, the body is formed in a square shape with one open side, including a fixing part to which the probe is fixed, and supporting parts extending from two ends of the fixing part in an extension direction of the probe.

According to another aspect of the present disclosure, there is provided a neural probe assembly including the neural probe structure, wherein the neural probe structure is fixed to the nerve such that the probe passes through the nerve, and the body encloses at least a part of circumference of the nerve.

According to an embodiment, the neural probe assembly includes a plurality of neural probe structures, the plurality of neural probe structures is fixed to the nerve such that the neural probe structures are arranged side by side along a lengthwise direction of the nerve, and the probes of each neural probe structure are inserted into the nerve such that the probes are oriented in different directions.

According to an embodiment, the probes of adjacent neural probe structures are inserted into the nerve, forming an angle of 90° therebetween when viewed in the lengthwise direction of the nerve.

According to an embodiment, the plurality of neural probe structures is bound together by a suture after the neural probe structures are fixed to the nerve.

According to an embodiment, the neural probe assembly further includes a spacer placed between the plurality of neural probe structures.

According to an embodiment, the body of the neural probe structure has a shape of a thin plate, and the neural probe assembly further includes a cover which encloses the neural probe structure fixed to the nerve in order to fix the neural probe structure while preventing the neural probe structure from being inclined in a lengthwise direction of the nerve.

According to an embodiment, the body of the neural probe structure has a polygonal shape, and the cover has an engaging part into which corners of the body are inserted.

According to an embodiment, the engaging part is placed radially when viewed in the lengthwise direction of the nerve.

According to an embodiment, the cover is made of an elastic material, and has a hollow shape with a cutout in the lengthwise direction of the nerve on one side.

DETAILED DESCRIPTION

Hereinafter, preferred embodiments of the present disclosure will be described with reference to the accompanying drawings. The present disclosure is described with reference to the embodiments shown in the drawings, but this is provided for illustration, and the technical spirit of the present disclosure and its key elements and operation are not limited thereby.

Figure 1:
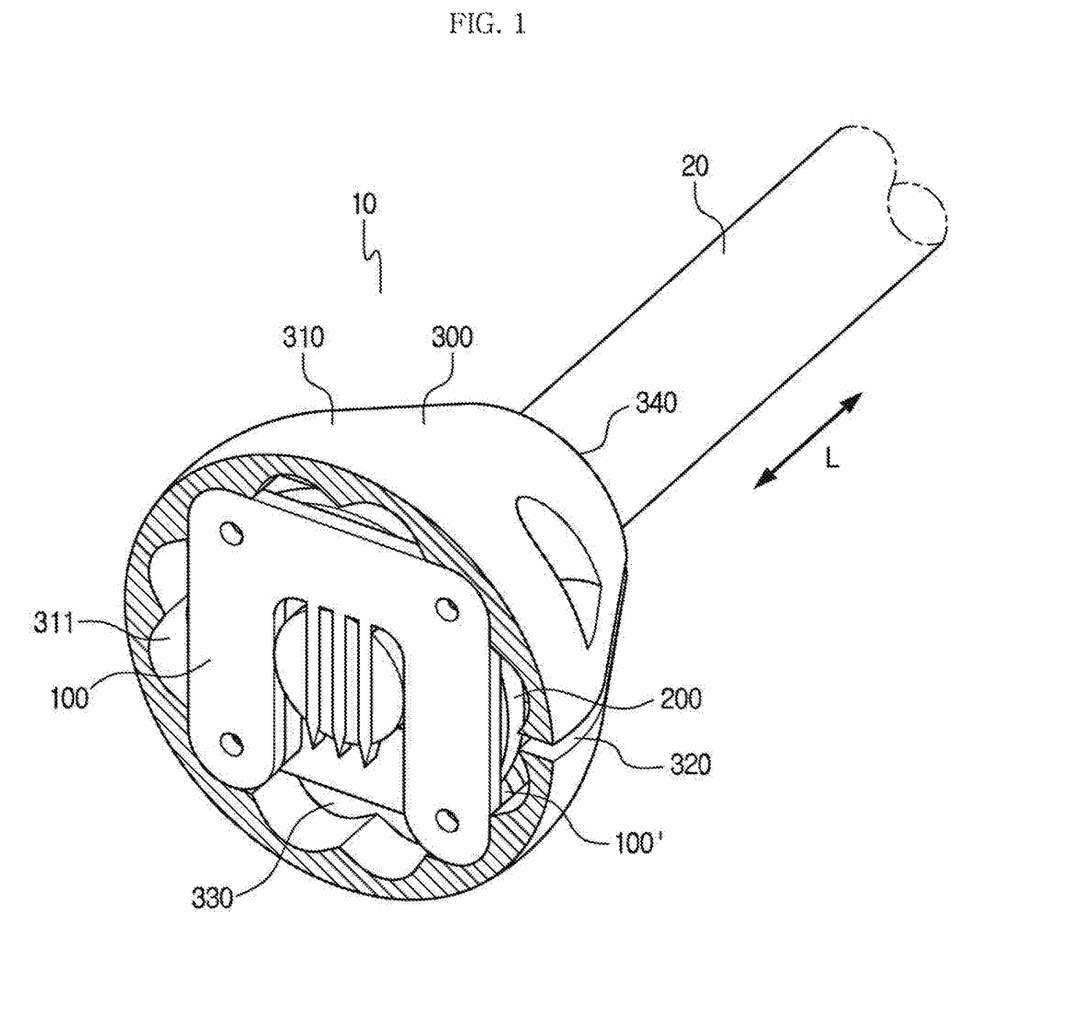
FIG. 1 shows a neural probe assembly according to an embodiment of the present disclosure.

FIG. 1 shows a neural probe assembly 10 according to an embodiment of the present disclosure. In FIG. 1, a cover 300 is shown as being cut in the radial direction for convenience of description.

According to this embodiment, the neural probe assembly 10 includes a plurality of neural probe structures 100, 100' formed to be fixed to a nerve 20, a spacer 200 installed between the adjacent neural probe structures 100, 100', and a cover 300 which encloses the neural probe structures 100, 100' and the spacer 200 in an inner space 330.

Figure 2:
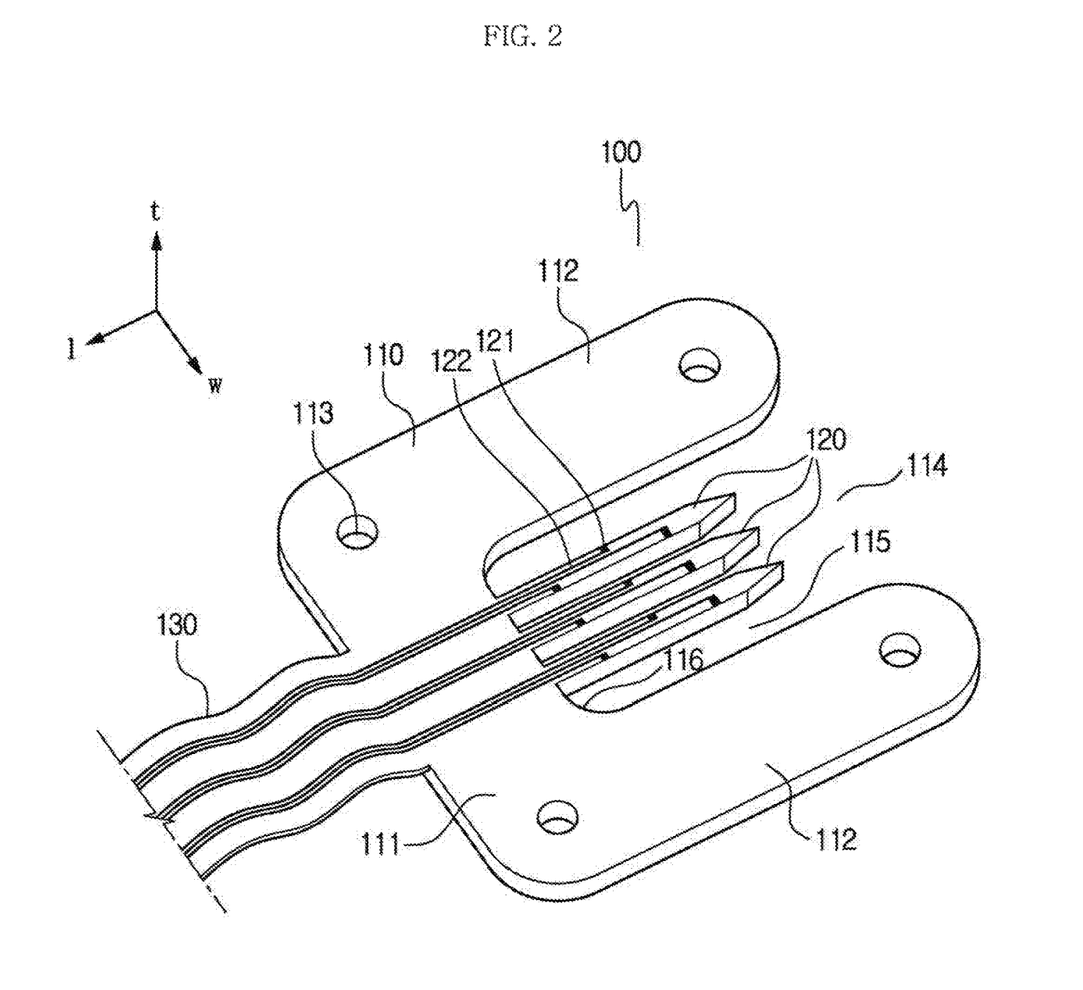
FIG. 2 shows a neural probe structure according to an embodiment of the present disclosure.

FIG. 2 shows the neural probe structure 100 according to an embodiment of the present disclosure.

As shown in FIG. 2, the neural probe structure 100 includes a body 110, and a plurality of probes 120 extending longitudinally from the body 110.

The body 110 of the neural probe structure 100 is bent to enclose at least a part of the circumference of the nerve 20. The term "enclose" as used herein should be understood as the body enclosing the nerve in contact with the circumference of the nerve as well as apart from the circumference of the nerve in whole or in part.

The body 110 of the neural probe structure 100 according to this embodiment has a square shape as a whole. Furthermore, the body 110 has an approximately "⊏" shape with an opening 114 on one side, including a fixing part 111 to which the probes 120 are fixed, and two supporting parts 112 extending from two ends of the fixing part 111 in the extension direction of the probes 120. The body 110 has a seating groove 115 which is cut as much as a predetermined area from the opening 114 to allow the nerve 20 to be seated.

The body 110 of the neural probe structure 100 has a shape of a thin plate with a thickness defining a thickness-wise direction t that is much greater than a width defining a widthwise direction w.

The probes 120 extend within the seating groove 115, and extend from one side surface 116 of the fixing part 111 toward the opening 114.

According to this embodiment, the body 110 of the neural probe structure 100 has an approximately "⊏" shape, but is not limited thereto. If the body has such a shape that it is bent to enclose at least a part of the circumference of the nerve 20, the body of the neural probe structure 100 may have, for example, a different polygonal shape with one open side, and may have a curved shape like the letter "C".

The body 110 of the neural probe structure 100 may have slight elasticity, and may be formed such that the width of the opening 114 and the seating groove 115 is smaller than the diameter of the nerve 20. However, according to this embodiment, for stable fixing and installation, the body 110 of the neural probe structure 100 has rigidity, and is formed such that the width of the opening 114 and the seating groove 115 is substantially equal to or slightly greater than the diameter of the nerve 20.

As shown in FIG. 2, the corners of the square body are rounded to avoid causing the body 110 of the neural probe structure 100 to damage tissues in the body.

Holes 113 for suture connection are formed near the corners of the square body 110.

According to this embodiment, the probes 120 are formed integrally with the body 110 such that they have the same thickness as the thickness of the body 110.

To broaden the scope of neural signal acquisition or electrical stimulation site, the neural probe structure 100 includes the plurality of probes 120. The plurality of probes 120 extends in the lengthwise direction I of the fixing part 111 and parallel to the supporting parts 112, and is arranged in rows side by side, spaced apart from each other in the widthwise direction w of the fixing part 111.

Electrodes 121 are formed on the upper surface of the probes 120 at different positions along the lengthwise direction of the probes 120 to acquire a neural signal or transmit electrical stimulation, and an electric wire 122 is connected to each electrode 121.

The electric wire 122 extends longitudinally over the upper surface of the fixing part 111 of the body 110 to a connector 130 connected to the rear end of the fixing part 111.

The connector 130 according to this embodiment is connected to the rear end part of the body 110, and is made of a flexible material so that it can freely bend and deform with respect to the body 110. The connector 130 to which a PCB substrate (not shown) is connected enables it to collect and process signals detected from the electrodes 121. In case that the neural probe structure 100 is constructed as a wireless module having a wireless communication chip embedded in the body 110, the connector 130 may be omitted. In the drawings other than FIG. 2, the illustration of the connector 130 is omitted.

Figure 3:
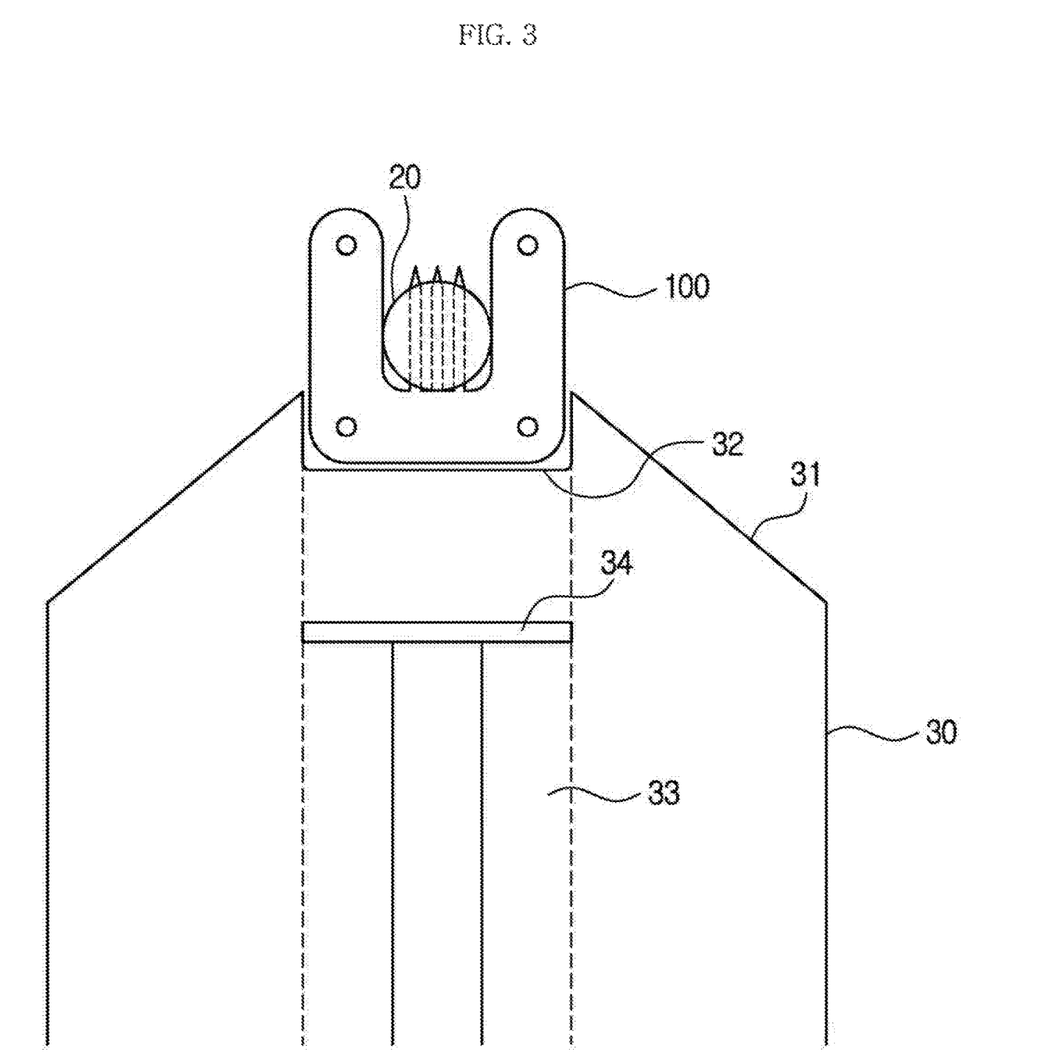
FIG. 3 shows fixing of the neural probe structure of FIG. 2 to a nerve using an insertion device.

FIG. 3 shows fixing of the neural probe structure 100 to the nerve 20 using an insertion device 30. It should be understood that the insertion device 30 is conceptually shown in FIG. 3.

Referring to FIG. 3, the insertion device 30 has, at a front end 31, a slit 32 that fits the width of the neural probe structure 100, and a path 33 inside to induce the neural probe structure 100 to move ahead. A piston 34 is formed within the path 33, and the neural probe structure 100 is forced to move ahead through the piston 34 so that the probes 120 pass through the nerve 20, thereby fixing the neural probe structure 100 to the nerve 20.

According to this embodiment, as shown in FIG. 3, the neural probe structure 100 is fixed to the nerve such that one side surface 116 defining the thickness of the fixing part 111 stands in contact with the circumferential surface of the nerve 20.

In this instance, the fixing part 111 and the supporting parts 112 of the body 110 support the circumference of the nerve 20 on three sides to provide a predetermined amount of fixing strength for stably fixing the neural probe structure 100 to the nerve 20.

With the single neural probe structure 100 alone, the probes 120 can be stably fixed to the nerve 20, and signal acquisition and/or electrical stimulation can be performed on the nerve 20 with excellent selectivity and scope.

To provide higher selectivity and fixing strength, the neural probe assembly 10 is constructed using the plurality of neural probe structures 100, 100' according to this embodiment.

FIGS. 4A to 4E are diagrams illustrating a process for forming the neural probe assembly 10 of FIG. 1.

Figure 4A:
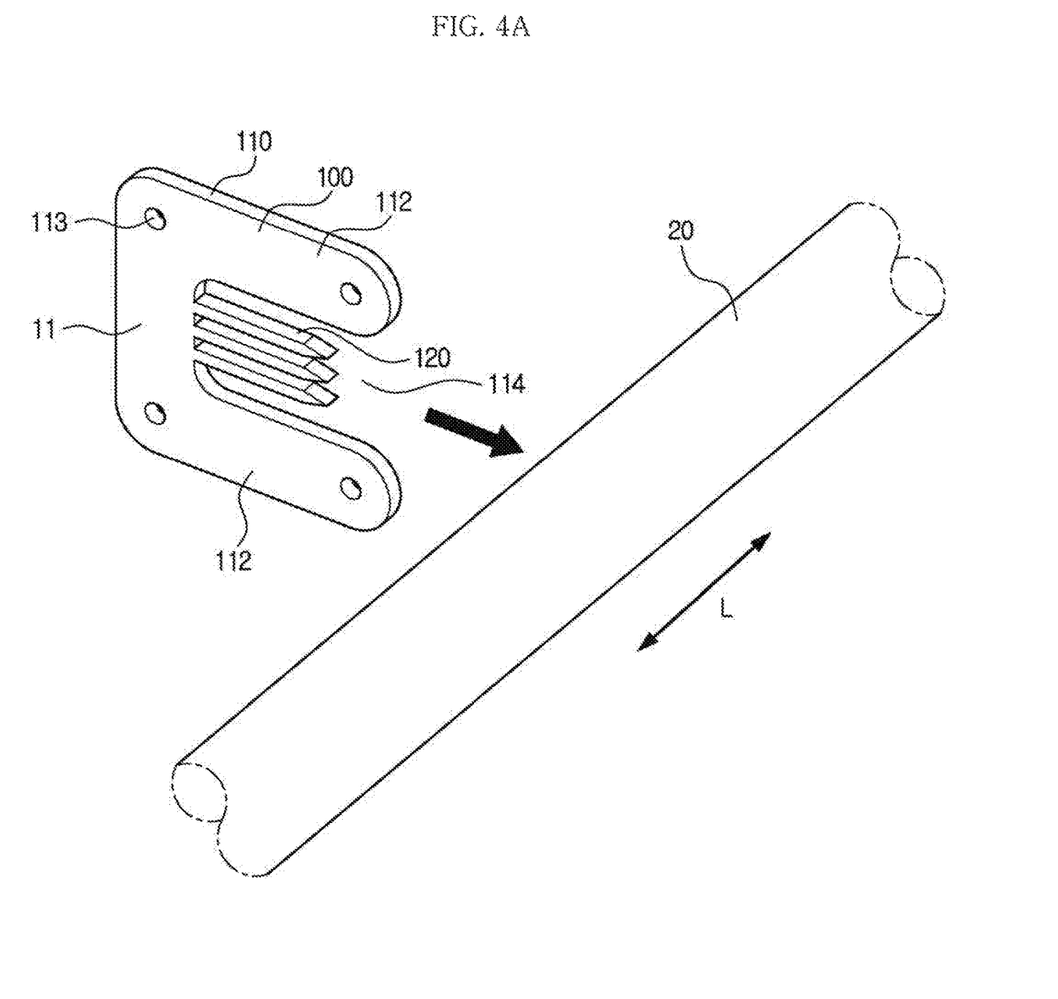
FIGS. 4A to 4E are diagrams illustrating a process for forming the neural probe assembly of FIG. 1.

As shown in FIG. 4A, one neural probe structure 100 is fixed to the nerve 20 first. As shown in FIG. 4A, the neural probe structure 100 approaches the nerve 20 in the direction in which the opening 114 of the body 110 faces the nerve 20, and the probes 120 pass through the nerve 20, and thereby the neural probe structure 100 is fixed to the nerve 20.

Figure 4B:
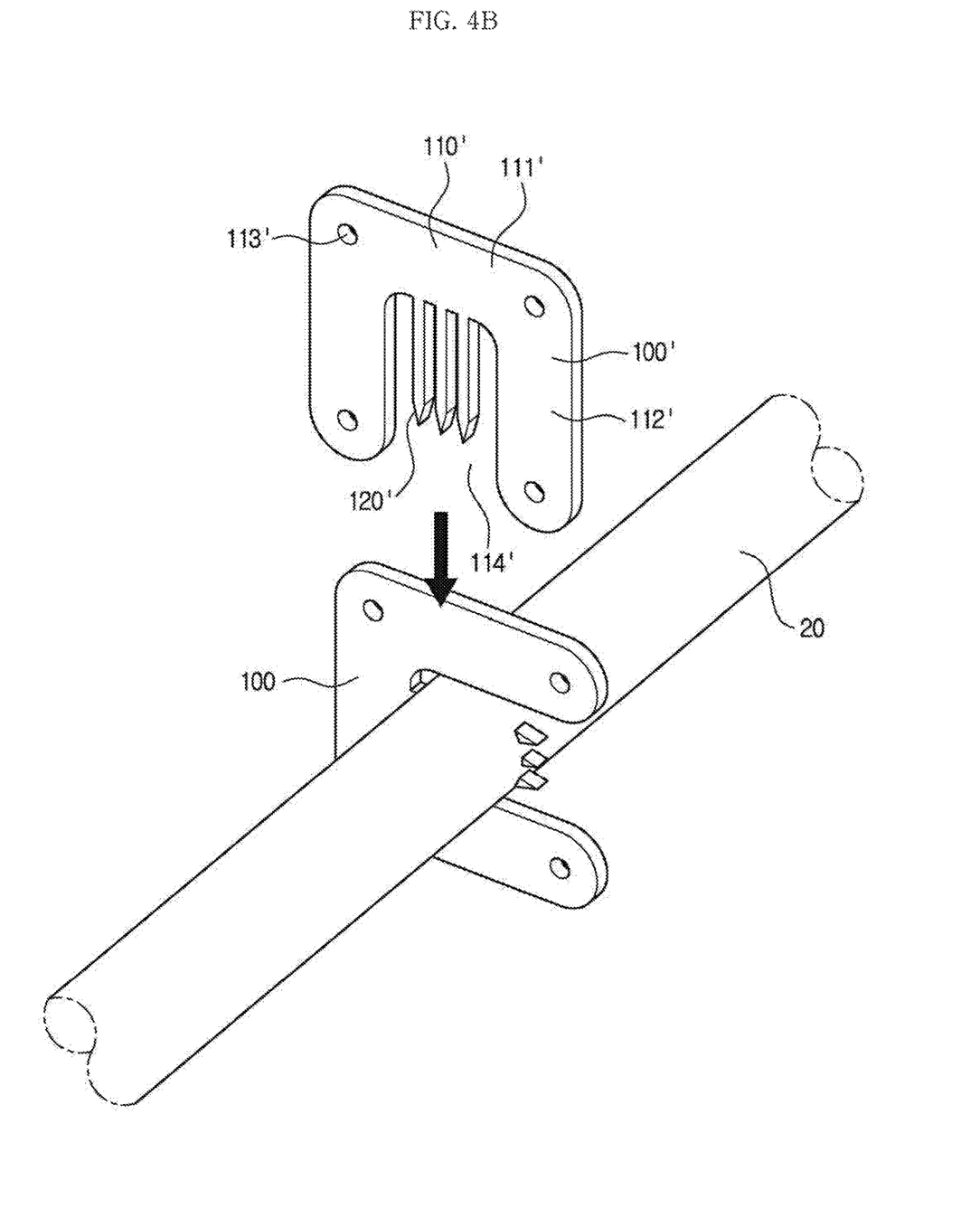

Subsequently, as shown in FIG. 4B, the other neural probe structure 100' is fixed to the nerve 20. The neural probe structure 100' is configured identically to the neural probe structure 100. In the drawings, the prime symbol (') is attached to reference signs designating the neural probe structure 100' and its elements, but this is for distinguishing the neural probe structure 100' from the neural probe structure 100, and it should be understood that elements indicated by the same figure are substantially the same element throughout the drawings.

Figure 4C:
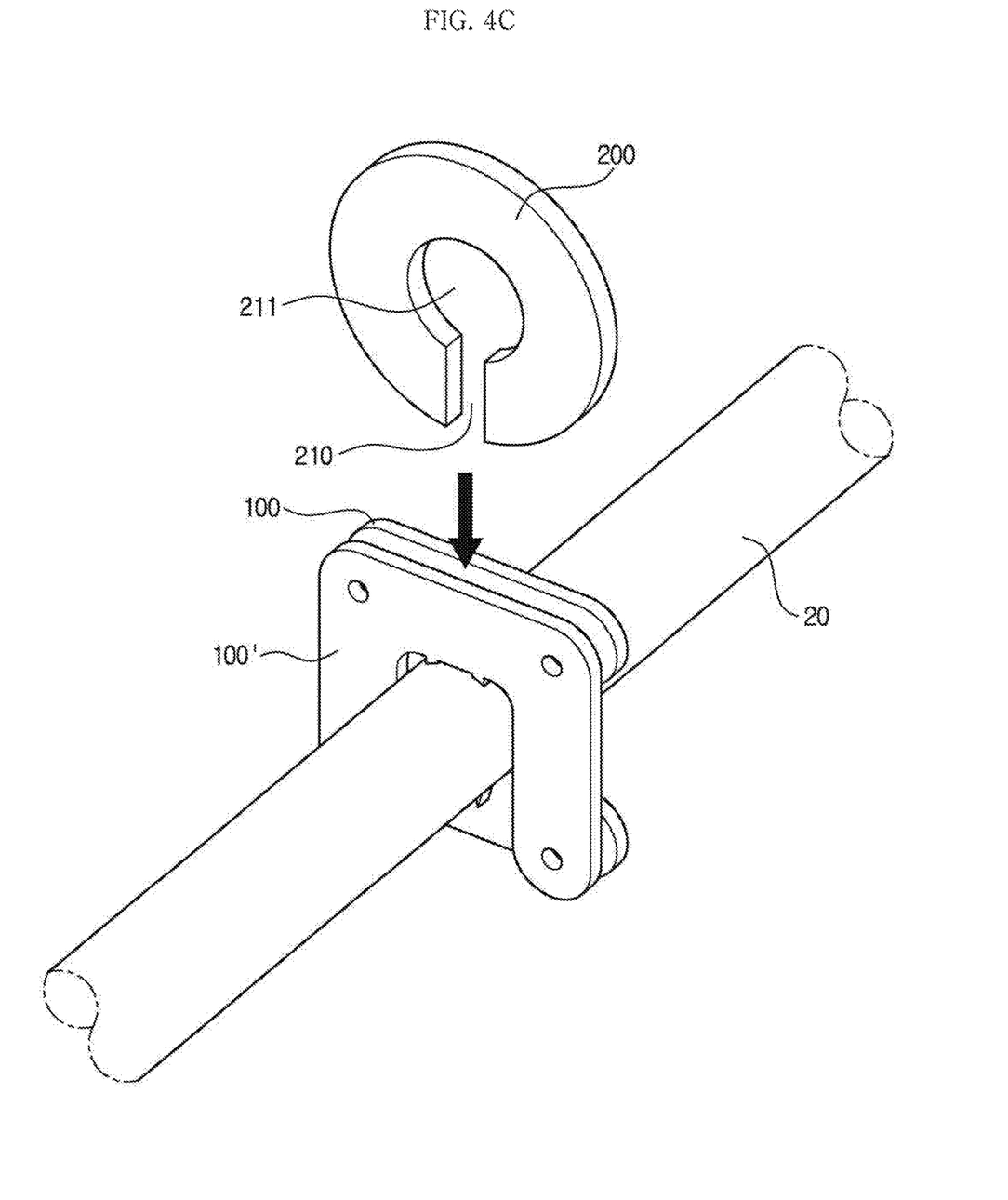

According to this embodiment, the neural probe structure 100' is fixed to the nerve such that it is placed parallel to the neural probe structure 100 along the lengthwise direction L of the nerve 20 (see FIG. 4C). In this instance, as shown in FIG. 4B, the probes 120, 120' of each neural probe structure 100, 100' are inserted into the nerve such that they are oriented in different directions. According to this embodiment, the probes 120, 120' of the adjacent two neural probe structures 100, 100' are inserted into the nerve 20, forming an angle of 90° therebetween when viewed in the lengthwise direction L of the nerve 20.

This task may be performed, for example, by fixing one neural probe structure 100, turning the insertion device 30 by 90°, and fixing the other neural probe structure 100', or otherwise, by fixing one neural probe structure 100, turning the nerve 20 by 90°, and fixing the other neural probe structure 100'. The corresponding task may be differently selected depending on operation environment or conditions.

It is preferred that two neural probe structures 100, 100' in close contact with each other are fixed to the nerve 20, but in practice, it may be difficult to bring the two neural probe structures 100, 100' into close contact and fix them.

Thus, according to this embodiment, as shown in FIG. 4C, the neural probe assembly 10 includes the spacer 200 which is inserted between the two neural probe structures 100, 100'.

The spacer 200 includes a cutout part 210 for insertion into the nerve 20, and an installation part 211 that approximately fits the diameter of the nerve 20 at the center. The spacer 200 according to this embodiment is made of an elastic material (for example, biocompatible rubber), and is designed to be inserted into the nerve 20 with the cutout part 210 slightly open when installing.

Preferably, the width of the spacer 200 is substantially the same as the size of a gap between the two neural probe structures 100, 100' that is expected to create during operation, but even when the width of the spacer 200 is slightly larger or smaller than the corresponding gap, a target function can be performed.

When the probes 120, 120' of the adjacent two neural probe structures 100, 100' are inserted into the nerve 20, forming an angle of 90° therebetween, the bodies 110, 110' of the two neural probe structures 100, 100' are also placed with one rotated 90° with respect to the other. Accordingly, as shown in FIG. 4C, the directions of the openings of 114, 114' of the neural probe structures 100, 100' through which the nerve 20 enters the seating grooves also have a relationship in which one is rotated 90° with respect to the other.

In other words, when the two neural probe structures 100, 100' fixed to the nerve 20 are viewed in the lengthwise direction L of the nerve 20, the two neural probe structures 100, 100' form a sort of a closed loop that completely encloses the circumference of the nerve 20.

Accordingly, when the two neural probe structures 100, 100' are bound together, even if the neural probe structure 100 makes a movement in the opposite direction to the opening 114, the movement is restrained by the neural probe structure 100'. Similarly, even if the neural probe structure 100' makes a movement in the opposite direction to the opening 114', the movement is restrained by the neural probe structure 100.

Movements in a direction in which the opening is not formed are restrained by the contact between the fixing part and the supporting parts of each neural probe structure and the circumference of the nerve, and as a result, the two neural probe structures 100, 100' bound together are kept in fixed position to the nerve because their movements are restrained in four directions. Accordingly, the probes 120, 120' are kept in fixed position to the nerve 20 firmly, making it possible to prevent damage that may occur to the nerve due to separation of the neural probe structures from the nerve or movement of the neural probe structures.

Figure 4D:
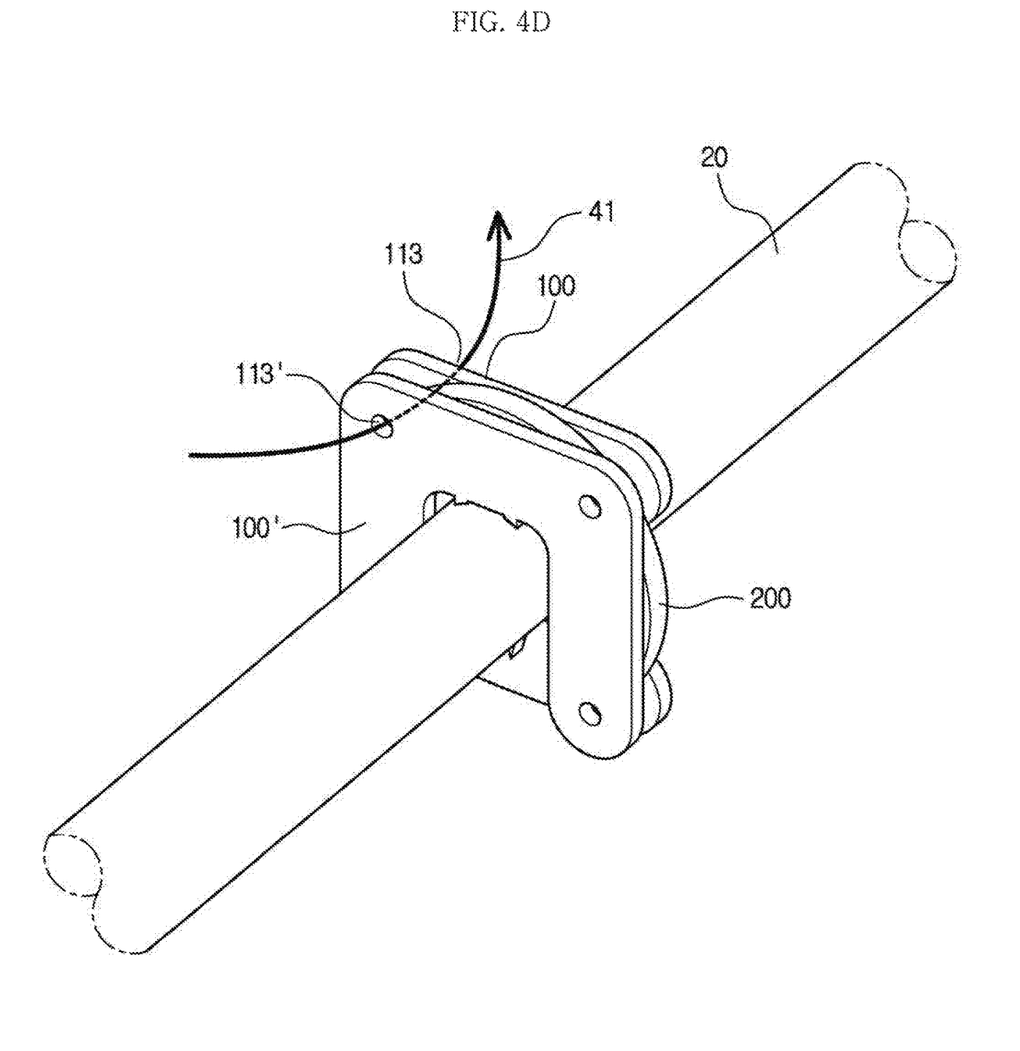

FIG. 4D shows binding of the two neural probe structures 100, 100'.

As described above, because the bodies 110, 110' of the two neural probe structures 100, 100' according to this embodiment have a square shape, even though the neural probe structures 100, 100' have a relationship in which one is rotated 90° with respect to the other, the bodies 110, 110' exactly overlap with each other when viewed in the lengthwise direction L of the nerve 20. Accordingly, the two neural probe structures 100, 100' may be bound together via a task of threading a suture 41 through the holes 113, 113' of the two neural probe structures 100, 100'.

When the neural probe assembly 10 is constructed using the two neural probe structures 100, 100' as described above, a stronger fixing strength than the case using the single neural probe structure can be obtained, and selectivity and scope for neural signals and stimulation can be greatly increased.

However, because the neural probe structure according to this embodiment has a shape of a thin plate and is fixed such that it stands against the circumference of the nerve 20, the neural probe structure 100 may be inclined in the lengthwise direction of the nerve 20 by friction with another tissue or the moment round the center of gravity of the neural probe structure ("slip phenomenon").

By this phenomenon, the probes 120 may damage the nerve 20, causing pain in the subject.

Figure 4E:
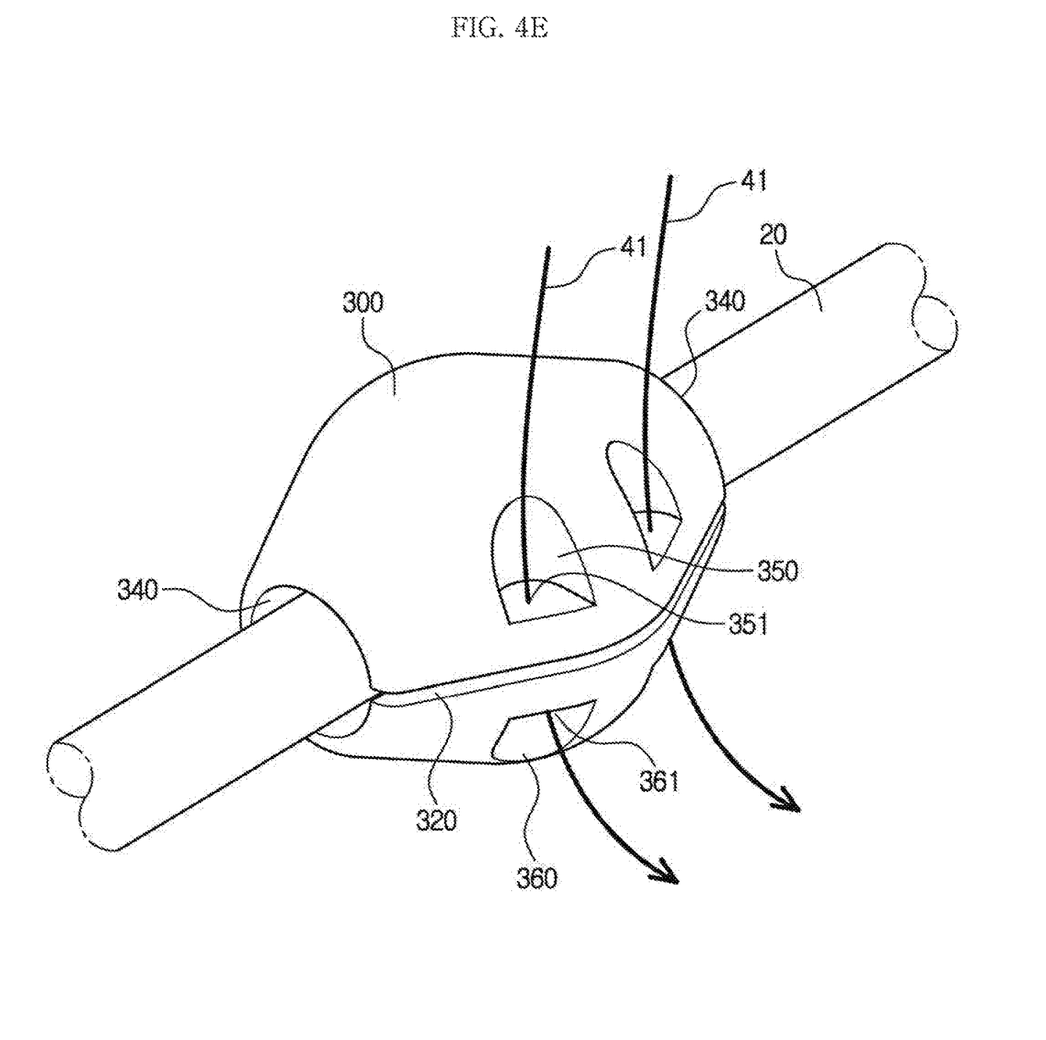

Thus, according to this embodiment, as shown in FIG. 4E, the neural probe assembly 10 includes the cover 300 to prevent the slip phenomenon of the neural probe structure.

The cover 300 encloses the neural probe structures 100, 100' fixed to the nerve 20, to fix the neural probe structures 100, 100' while preventing the neural probe structures 100, 100' from being inclined in the lengthwise direction L of the nerve 20.

The cover 300 according to this embodiment has an approximately rugby ball-shaped hollow shape. The cover 300 has sufficient diameter and length to completely enclose the neural probe structures 100, 100' and the spacer 200. Although this embodiment describes that the cover 300 encloses the plurality of neural probe structures and the spacer, it should be understood that a slip phenomenon may occur even in case that the single neural probe structure is used, and the cover 300 may be configured to accommodate the single neural probe structure 100.

Figure 5:
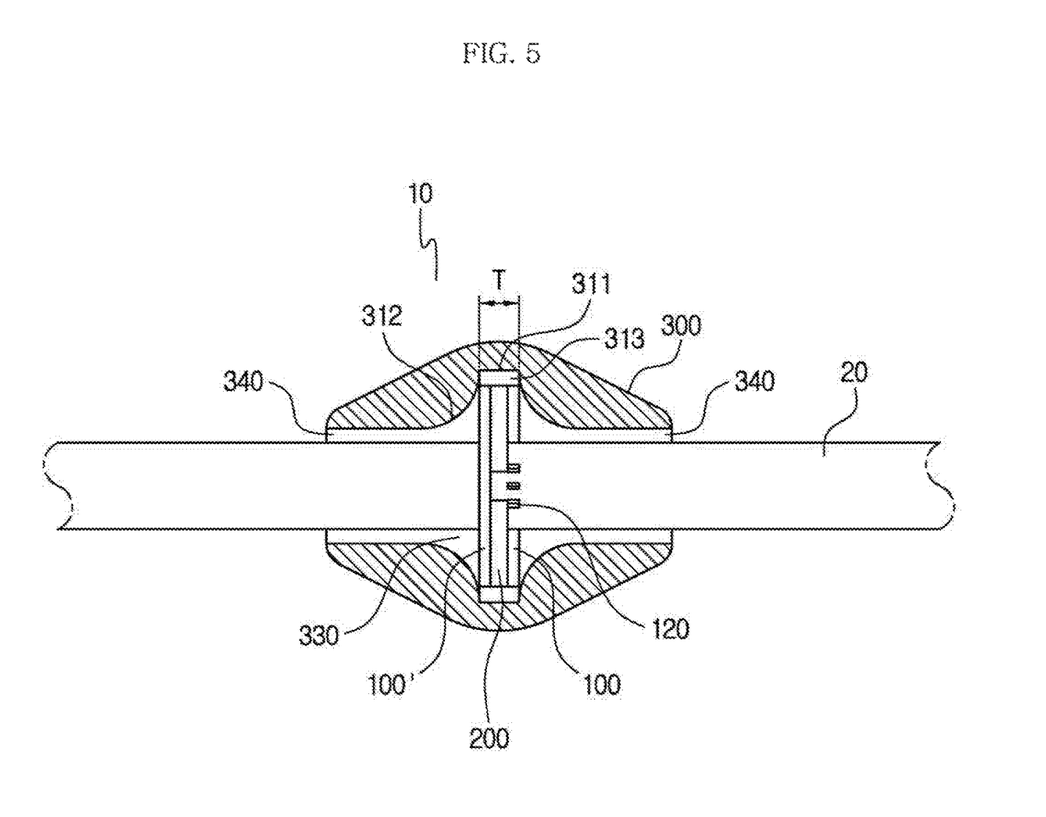
FIG. 5 is a cross-sectional view of the neural probe assembly of FIG. 1 in which a cover is shown as being cut in the lengthwise direction.

FIG. 5 is a cross-sectional view of the neural probe assembly 10 in which the cover 300 is shown as being cut in the lengthwise direction.

Referring to FIGS. 1 and 5, the cover 300 has a hollow shape with a cutout part 320 cut in the lengthwise direction L of the nerve 20 on one side. The cover 300 is made of an elastic material, and may completely enclose the neural probe structures 100, 100' and the spacer 200 in a manner of opening the cutout part 320, receiving the neural probe structures 100, 100' and the spacer 200 in the inner space 330, and closing the cutout part 320.

Openings 340 larger than the diameter of the nerve 20 are formed at the left and right ends of the cover 300, and the nerve 20 goes through the cover 300 and extends via the openings 340. Accordingly, the cover 300 is not directly fixed to the nerve 20, and is fixed in position spaced apart from the nerve 20 by the neural probe structures 100, 100'.

Although not shown, the connector 130 of the neural probe structure 100 may be appropriately bent and exposed to the outside through the opening 340 of the cover 300. Alternatively, a slit that fits the width of the connector 130 may be formed through the cover 300 at an appropriate position of the cover 300, so that the connector 130 may go outward through the slit.

The inner space 330 is formed within the cover 300 to receive the neural probe structures 100, 100' and the spacer 200. As best shown in FIG. 5, the inner space 330 includes a seating part 313 having approximately the same width T as the sum of the widths of the neural probe structures 100, 100' and the spacer 200, and a convex part 312 formed convexly at the side of the neural probe structures 100, 100' to support the outward rotation of the neural probe structures 100, 100'.

The inclination of the neural probe structures 100, 100' in the lengthwise direction of the nerve 20 is prevented by support of the seating part 313 and the convex part 312, thereby preventing a slip phenomenon.

As shown in FIG. 1, the seating part 313 has engaging parts 311 into which the round corners of the body of the neural probe structure can be inserted. According to this embodiment, the engaging parts 311 of the same shape are arranged radially when viewed in the lengthwise direction L of the nerve 20 to form a groove as if it has a serrated shape.

Accordingly, a relative location of the cover 300 to the neural probe structures 100, 100' can be freely selected, thereby overcoming the limitation on operation space.

As shown in FIG. 4E, binding parts 350, 360 are formed above and below the cutout part 320 of the cover 300, and the binding parts 350, 360 have holes 351, 361 through which the suture 41 can be threaded. After the cover 300 is mounted, the cutout part 320 of the cover 300 is closed using the suture 41.

Because the two neural probe structures 100, 100' are brought into close contact with each other by the cover 300, the binding process of the two neural probe structures 100, 100' by the suture 41 may be omitted according to necessity, and in this case, the neural probe structures may not have the holes 113, 113'.

On the other hand, in the above embodiment, the spacer 200 is placed between the neural probe structures 100, 100', but is not limited thereto.

The spacer 200 brings the neural probe structures 100, 100' into close contact with each other through the spacer, and this function can be also achieved through the shape of the cover 300.

Figure 6:
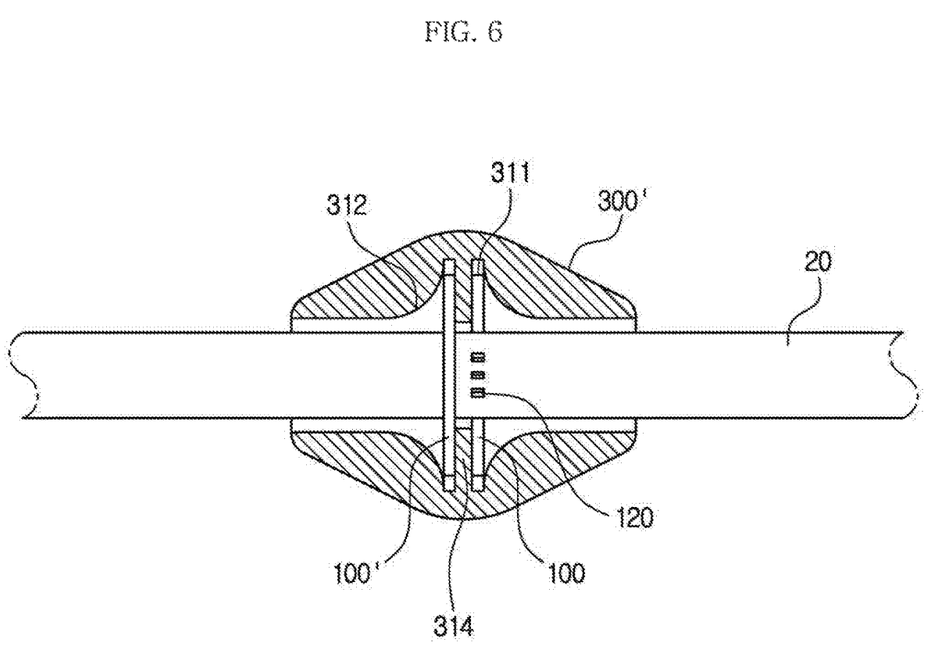
FIG. 6 is a cross-sectional view of a neural probe assembly including a cover according to another embodiment.

As shown in FIG. 6, according to another embodiment of the present disclosure, the cover 300 may include a protrusion 314 with an approximately ring shape in the inner space 330. The protrusion 314 is disposed between the two neural probe structures 100, 100' to replace the function of the spacer 200 (the process of FIG. 4C can be omitted).

With the neural probe structure and the neural probe assembly according to this embodiment, the electrodes can be firmly fixed within the nerve while minimizing damage to the nerve, allowing for appropriate neural signal acquisition and/or stimulation delivery.

The neural probe assembly according to this embodiment includes the neural probe structure which is a single module in a shape of a thin flat plate, and thus, has a structure that can be readily changed depending on a necessary nerve part for neural signal acquisition and/or electrical stimulation, by binding the neural probe structures with addition or subtraction of the neural probe structures according to necessity.

What is claimed is:

1. A neural probe structure configured to be fixed to a nerve to acquire an electrical signal from the nerve or apply an electrical stimulation to the nerve, the neural probe structure comprising:
    a body configured to extend around at least a part of a circumference of the nerve; and
    a probe extending longitudinally from the body and configured to pass through the nerve,
    wherein the body has a shape of a thin flat plate, and
    wherein the neural probe structure is configured to be fixed to the nerve such that one side surface defining a thickness of the body stands facing a circumferential surface of the nerve.

2. The neural probe structure according to claim 1, wherein the body of the neural probe structure has a polygonal shape with one open side, and
    wherein the body has rounded corners.

3. The neural probe structure according to claim 1, wherein the body is formed in a square shape with one open side, comprising a fixing part to which the probe is fixed, and supporting parts extending from two ends of the fixing part in an extension direction of the probe.

4. The neural probe structure according to claim 1, wherein the body of the neural probe structure has holes therein for suture connection.

5. The neural probe structure according 3, wherein the neural probe structure comprises a plurality of probes,
    wherein each of the plurality of probes has electrodes, and
    wherein each of the plurality of probes is arranged in rows side by side in a widthwise direction of the body.

6. A neural probe assembly comprising:
    the neural probe structure according to claim 1; and
    a cover enclosing the neural probe structure.

7. The neural probe assembly according to claim 6, wherein the neural probe assembly comprises a plurality of the neural probe structures, wherein the plurality of neural probe structures are arranged side by side, and wherein probes of each of the plurality of neural probe structures are oriented in different directions.

8. The neural probe assembly according to claim 7, wherein probes of adjacent neural probe structures form an angle of 90° therebetween.

9. The neural probe assembly according to claim 7, wherein the plurality of neural probe structures each include a plurality of holes therein configured to receive a suture therethrough.

10. The neural probe assembly according to claim 7, further comprising a spacer located between the plurality of neural probe structures.

11. The neural probe assembly according to claim 10, wherein the spacer comprises:

an installation part at the center of the spacer, the installation part being configured to extend around at least a part of the circumference of the nerve; and a cutout part extending outward from the installation part, wherein the spacer is made of an elastic material.

12. The neural probe assembly according to claim 7, wherein the cover includes a protrusion in an inner space of the cover, the protrusion being positioned between the plurality of neural probe structures.

13. The neural probe assembly according to claim 6, wherein the cover has an engaging part therein into which corners of the body of the neural probe structure are inserted.

14. The neural probe assembly according to claim 13, wherein the engaging part extends radially with respect to a lengthwise direction of the cover.

15. The neural probe assembly according to claim 6, wherein the cover is made of an elastic material, and wherein the cover has a hollow shape with a cutout in a lengthwise direction of the cover.

* * * * *